(12) United States Patent
Neel et al.

(10) Patent No.: US 8,636,672 B2
(45) Date of Patent: Jan. 28, 2014

(54) TEST STRIP WITH INTEGRATED LANCET

(75) Inventors: Gary Neel, Weston, FL (US); Allan Javier Caban, Lake Worth, FL (US)

(73) Assignee: Nipro Diagnostics, Inc., Fort Lauderdale, FL (US)

( * ) Notice: Subject to any disclaimer, the term of this patent is extended or adjusted under 35 U.S.C. 154(b) by 223 days.

(21) Appl. No.: 11/711,621

(22) Filed: Feb. 28, 2007

(65) Prior Publication Data

US 2008/0208078 A1    Aug. 28, 2008

(51) Int. Cl.
*A61B 5/151* (2006.01)
*A61B 5/15* (2006.01)

(52) U.S. Cl.
CPC ..................................... *A61B 5/1411* (2013.01)
USPC ........................................................ 600/583

(58) Field of Classification Search
USPC ................................................. 600/583, 584
See application file for complete search history.

(56) References Cited

U.S. PATENT DOCUMENTS

| | | | |
|---|---|---|---|
| 4,627,445 A | 12/1986 | Garcia et al. | |
| 4,637,403 A | 1/1987 | Garcia et al. | |
| 4,769,261 A * | 9/1988 | Hazelton et al. | 428/35.3 |
| 4,787,398 A | 11/1988 | Garcia et al. | |
| 4,790,979 A | 12/1988 | Terminiello et al. | |
| 4,892,097 A | 1/1990 | Ranalletta et al. | |
| 5,029,583 A | 7/1991 | Meserol et al. | |
| 5,700,695 A | 12/1997 | Yassinzadeh et al. | |
| 5,962,333 A | 10/1999 | Incorvia et al. | |
| 6,099,484 A | 8/2000 | Douglas et al. | |
| 6,210,420 B1 | 4/2001 | Mauze et al. | |
| 6,315,738 B1 | 11/2001 | Nishikawa et al. | |
| 6,472,220 B1 | 10/2002 | Simons et al. | |
| 6,540,762 B1 | 4/2003 | Bertling | |
| 6,541,266 B2 | 4/2003 | Modzelewski et al. | |
| 6,561,989 B2 | 5/2003 | Whitson | |
| 6,620,112 B2 | 9/2003 | Klitmose | |
| 6,840,912 B2 | 1/2005 | Kloepfer et al. | |
| 6,862,465 B2 | 3/2005 | Shults et al. | |
| D506,832 S | 6/2005 | Neel et al. | |
| D507,657 S | 7/2005 | Neel et al. | |
| 6,966,880 B2 | 11/2005 | Boecker et al. | |

(Continued)

FOREIGN PATENT DOCUMENTS

DE    2422260 A1    11/1975
DE    2834330        2/1979

(Continued)

OTHER PUBLICATIONS

International Search Report for PCT/US2008/054995, Mailed Aug. 6, 2008.

*Primary Examiner* — Sean Dougherty
*Assistant Examiner* — Michael C Stout
(74) *Attorney, Agent, or Firm* — Finnegan, Henderson, Farabow, Garrett & Dunner

(57) ABSTRACT

The present disclosure provides methods and systems to collect blood from a patient using a lancet integrated with a test strip. The present disclosure provides integrated test strips having an integrated lancet, as well as meters for actuating the lancet integrated within a test strip. The analyte test strip comprises a first test strip substrate material and a second test strip substrate material. At least one test strip substrate material comprises an elongate cavity. The test strip further comprises a reaction test site for testing analyte concentrations in blood. The test strip further comprises at least one opening communicating with the at least one cavity.

12 Claims, 4 Drawing Sheets

(56) References Cited

U.S. PATENT DOCUMENTS

| | | |
|---|---|---|
| 7,001,344 B2 | 2/2006 | Freeman et al. |
| 7,025,774 B2 | 4/2006 | Freeman et al. |
| 7,041,468 B2 | 5/2006 | Drucker et al. |
| 7,049,130 B2 | 5/2006 | Carroll et al. |
| 7,136,689 B2 | 11/2006 | Shults et al. |
| 7,150,755 B2 | 12/2006 | Levaughn et al. |
| 7,175,642 B2 | 2/2007 | Briggs et al. |
| 7,264,627 B2 | 9/2007 | Perez |
| 7,645,241 B2 | 1/2010 | Roe |
| 7,727,474 B2 | 6/2010 | Krause |
| 7,935,063 B2 | 5/2011 | Roe |
| 7,955,271 B2 | 6/2011 | Roe et al. |
| 8,083,760 B2 * | 12/2011 | List ................................ 606/181 |
| 2002/0103499 A1 * | 8/2002 | Perez et al. ..................... 606/182 |
| 2002/0120216 A1 * | 8/2002 | Fritz et al. ...................... 600/583 |
| 2002/0168290 A1 | 11/2002 | Yuzhakov et al. |
| 2002/0188223 A1 * | 12/2002 | Perez et al. ..................... 600/573 |
| 2003/0050573 A1 * | 3/2003 | Kuhr et al. ...................... 600/567 |
| 2003/0078546 A1 * | 4/2003 | Jensen ............................ 604/232 |
| 2003/0083685 A1 * | 5/2003 | Freeman et al. ................ 606/181 |
| 2003/0144608 A1 * | 7/2003 | Kojima et al. .................. 600/583 |
| 2003/0223906 A1 * | 12/2003 | McAllister et al. ............. 422/58 |
| 2004/0034318 A1 * | 2/2004 | Fritz et al. ........................ 604/19 |
| 2004/0186394 A1 | 9/2004 | Roe et al. |
| 2004/0248312 A1 | 12/2004 | Vreeke et al. |
| 2005/0004494 A1 * | 1/2005 | Perez et al. ..................... 600/583 |
| 2005/0126653 A1 * | 6/2005 | Tachikawa et al. ............. 141/18 |
| 2005/0277850 A1 * | 12/2005 | Mace et al. ..................... 600/584 |
| 2006/0004303 A1 * | 1/2006 | Weidenhaupt et al. ........ 600/583 |
| 2006/0008389 A1 * | 1/2006 | Sacherer et al. ................ 422/102 |
| 2006/0030788 A1 * | 2/2006 | Wong et al. .................... 600/583 |
| 2006/0100543 A1 * | 5/2006 | Raney et al. .................... 600/583 |
| 2006/0116607 A1 * | 6/2006 | Nakamura et al. ............. 600/583 |
| 2006/0200045 A1 * | 9/2006 | Roe ................................. 600/583 |
| 2006/0241517 A1 * | 10/2006 | Fowler et al. .................. 600/583 |
| 2007/0100256 A1 | 5/2007 | Sansom |
| 2007/0123802 A1 | 5/2007 | Freeman |
| 2007/0276290 A1 | 11/2007 | Boecker et al. |
| 2008/0243032 A1 * | 10/2008 | Hindelang et al. ............ 600/583 |
| 2012/0035505 A1 * | 2/2012 | Fritz et al. ...................... 600/583 |

FOREIGN PATENT DOCUMENTS

| | | | |
|---|---|---|---|
| EP | 0 255 338 A2 | 2/1988 | |
| EP | 1 285 629 A1 | 2/2003 | |
| EP | 1 346 686 A2 | 9/2003 | |
| EP | 1982644 A1 | 10/2008 | |
| WO | WO 95/10977 | 4/2003 | |
| WO | WO 2004064636 A1 * | 8/2004 | ............... A61B 5/15 |

* cited by examiner

TEST STRIP WITH INTEGRATED LANCET

TECHNICAL FIELD

The present disclosure pertains to the field of diagnostic testing and, more particularly, to diagnostic testing systems using electronic analyte meters.

BACKGROUND

Electronic testing systems are commonly used to measure or identify one or more analytes in a sample. Such testing systems can be used to evaluate medical samples for diagnostic purposes and to test various non-medical samples. For example, medical diagnostic meters can provide information regarding the presence, amount, or concentration of various analytes in human or animal body fluids. In addition, diagnostic test meters can be used to monitor analytes or chemical parameters in non-medical samples such as water, soil, sewage, sand, air, or any other suitable sample.

Diagnostic testing systems typically include both a test medium, such as a diagnostic test strip, and a test meter configured for use with the test medium. Suitable test media may include a combination of electrical, chemical, and/or optical components configured to provide a response indicative of the presence or concentration of an analyte to be measured. For example, some glucose test strips include electrochemical components, such as glucose specific enzymes, buffers, and one or more electrodes. The glucose specific enzymes may cause a reaction between glucose in a sample and various chemicals on a test medium, thereby producing an electrical signal that can be measured with the one or more electrodes. The test meter can then convert the electrical signal into a glucose test result. Such enzymes may include glucose dehydrogenase, glucose oxidase, etc.

Diagnostic testing systems have improved significantly in recent years. For example, test meters have become smaller and faster, and the amount of blood or other fluid needed to obtain accurate test results has decreased. However, although these improvements have made testing more convenient for patients, current systems have some drawbacks. For example, current systems and devices for monitoring blood glucose levels in diabetic patients require patients to carry at least three devices: a lancet, a blood glucose meter, and test strips; and the need to carry three separate items can be inconvenient and cumbersome. In addition, carrying more components makes it easier to misplace or lose a component. Further, systems that employ separate lancets often include lancets that can be reused. However, reusing the same lancet is less sanitary than using a new, disposable lancet each time. In addition, repeated use of the same lancet can cause the lancet to become dull over time and cause more pain to the patient upon use.

While current methods and systems facilitate the self monitoring of analyte concentrations in blood or a bodily fluid, there is a need for additional features and improvements, including systems with fewer components. The present invention is directed at overcoming one or more shortcomings of the prior art of meters, lancets, and test strips.

SUMMARY OF THE INVENTION

The present disclosure provides methods and systems to collect blood from a patient using a lancet integrated with a test strip. In traditional systems, the various components of a blood collection system (i.e. meter, test strip, and lancet) are separate objects. However, the present disclosure provides integrated test strips having an integrated lancet, as well as meters for actuating the lancet integrated within a test strip.

In one aspect of the present disclosure, the test strip is composed of at least one test strip substrate and has an elongate cavity extending through at least one of the substrates. The cavity is adapted to receive a lancet and the test strip has an opening through which the lancet may be deployed. The test strip also comprises a reaction site where the patient's blood can be collected.

A second aspect of the present disclosure includes an analyte meter for monitoring a characteristic of a sample of blood. The meter can include an actuation mechanism configured to extend a lancet through an opening of a test strip and to retract the lancet after the lancet has pierced a patient's skin. The meter further includes a test strip interface for receiving a test strip on which a blood sample can be collected. In addition the meter includes a system for measuring the concentration of an analyte in a sample of blood.

A third aspect of the present disclosure includes integrating a test strip with a lancet. The method can include selecting a first test strip substrate material followed by selecting a second test strip substrate material. Next, at least one elongate cavity is formed in at least one of the first or second test strip substrate materials. Then, a lancet material is selected and cut into an elongate shape in order to fit into the elongate cavity formed in the at least one substrate materials. Finally, the lancet is disposed into the elongate cavity and the first and second substrate materials are mated to one another.

BRIEF DESCRIPTION OF THE DRAWINGS

The accompanying drawings, which are incorporated in and constitute a part of this specification, provide exemplary embodiments of the invention and, together with the description, serve to explain the principles of the invention.

DETAILED DESCRIPTION OF THE DRAWINGS

References will now be made in detail to the exemplary embodiments of the invention, examples of which are illustrated in the accompanying drawings. Wherever possible, the same reference numbers will be used throughout the drawings to refer to the same or like parts.

The present disclosure provides a test strip having an integrated lancet. This test strip with integrated lancet can be used to collect a sample of blood from a patient and then, in conjunction with an analyte meter, to measure the analyte content of the collected blood. In some embodiments, the test strip with integrated lancet can be mated with an analyte meter configured to actuate the lancet in order to pierce a patient's skin to collect a blood sample. Further, in some embodiments, the blood may be collected on the same test strip while still mated with the analyte meter in order to detect or measure an analyte in the blood.

Figure 1:
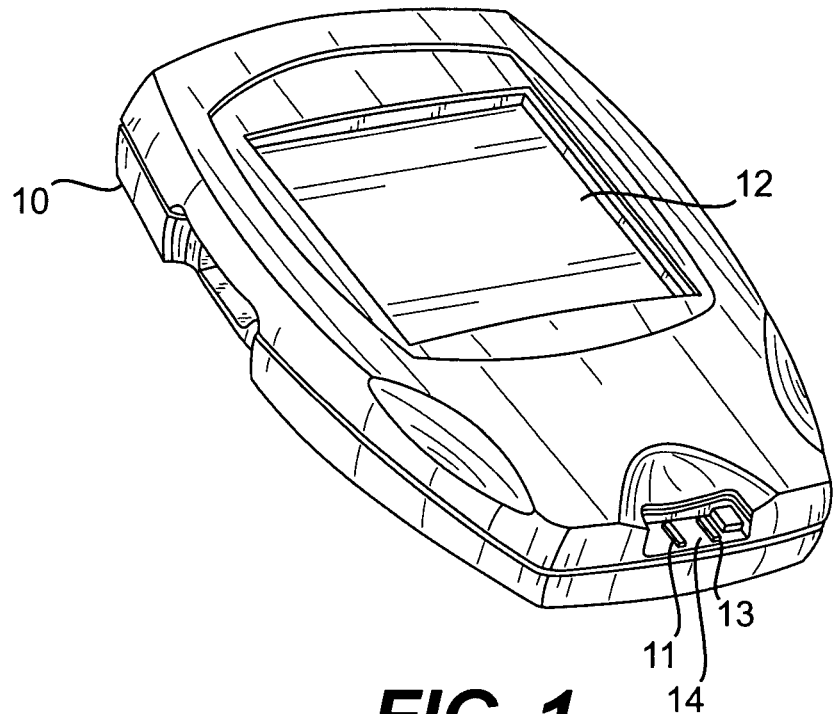
FIG. 1 illustrates a perspective view of an analyte meter, according to an exemplary disclosed embodiment.

FIG. 1 illustrates a perspective view of an analyte meter 10, according to an exemplary disclosed embodiment. The analyte meter 10 can be configured to measure or detect blood analytes and to display relevant information to a user. As shown in FIG. 1, the analyte meter 10 comprises several components, including a display system 12 and a test strip interface 14. Display system 12 can be configured to communicate test results to a user using visual and/or audio systems. Further, the test strip interface 14 may be configured to mate with a test strip 16 (shown in FIGS. 2A-2C) to secure the test strip to the meter 10. Further, the interface 14 can include one or more electrodes 11, 13 configured to form an electrical connection with a mated test strip.

The analyte meter 10 can be used to detect or measure the concentration of one or more analytes. The one or more analytes may include a variety of different substances, which may be found in biological samples, such as blood, urine, tear drops, semen, feces, gastric fluid, sweat, cerebrospinal fluid, saliva, vaginal fluids (including suspected amniotic fluid), culture media, and/or any other biologic sample. In some embodiments the biologic sample can include blood and the analyte can include glucose.

As noted, FIG. 1 also illustrates the test strip interface 14 having electrical meter components with one or more electrodes 11, 13. The test strip interface 14 can be configured to mate with the test strip 10, and the one or more electrodes 11 13 on the test strip interface 14 may be configured to engage electrical components of a test strip, thereby facilitating measurement of electrical signals, i.e. currents or voltages, which may be produced by an electrochemical reaction within a test strip reaction test site and may represent the concentration of an analyte within a collected sample. The one or more electrodes 11, 13 can include a number of electrode types and configurations. For example, the one or more electrodes 11, 13 can include a cathode 11 and an anode 13, as well as one or more additional electrodes. The specific number and type of electrodes may be selected based on the desired testing modality, the specific analyte meter type being used, and any other suitable parameter. Further, the one or more electrodes 11, 13 can include a number of shapes and configurations. For example, the one or more electrodes 11, 13 can include planar electrodes, interdigitated electrodes, or any other suitable electrode pattern. Further, it will be understood that although the disclosed integrated test strip 16 and lancet 18 are described for use with an electrical test meter 10, any suitable testing system may be used. For example, suitable meters can include electrochemical systems, optical systems, electrochemiluminescent systems, radioactive assays, and/or any other suitable system in which an integrated test strip may be desirable.

Figure 2A:
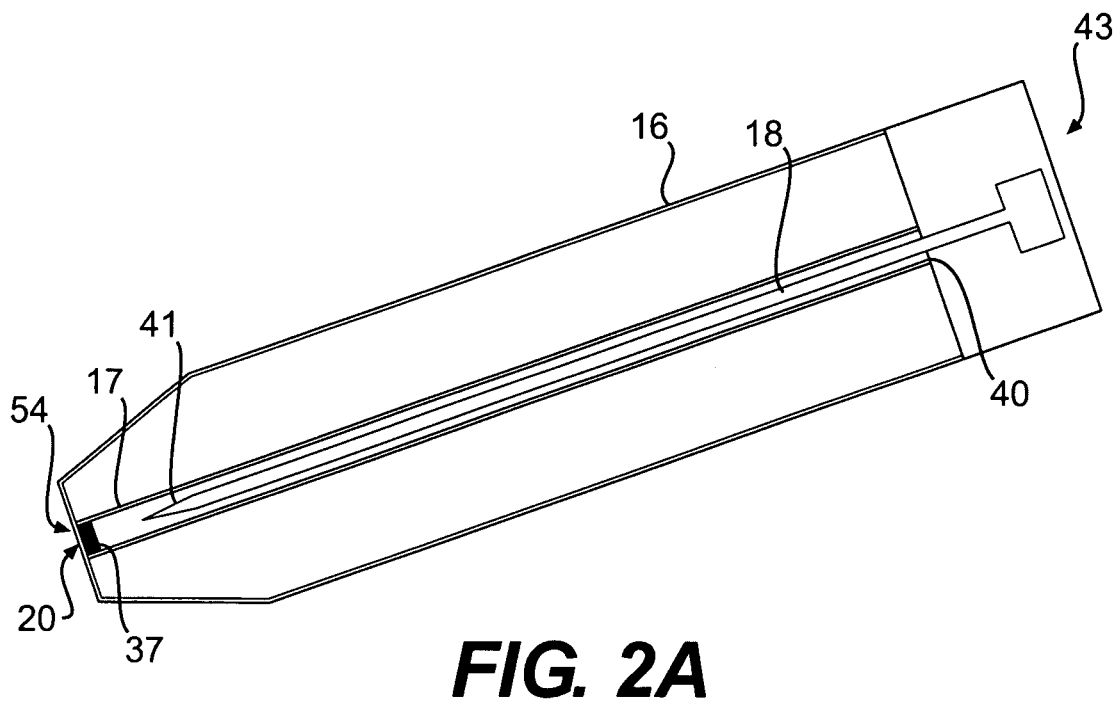
FIG. 2A illustrates a bottom view of a test strip, according to an exemplary disclosed embodiment.

FIG. 2A illustrates a bottom view of a test strip 16, according to an exemplary disclosed embodiment. As shown, the test strip 16, includes an elongate cavity 17 configured to hold a lancet 18. The test strip 16 also includes an opening 20 on one end 54 through which a sharp end 41 of the lancet may be advanced and retracted to pierce the skin of a patient proximate the opening 20. The test strip 16 may be configured to mate with a meter interface 14 at a second end 43 of the test strip 16. The second end 43 may further include one or more electrodes 27 (as shown in FIG. 2B) that can form an electrical connection with the meter electrodes 11, 13.

The test strip 16 may comprise a mechanism for adjusting the depth of penetration of the lancet 18. This may prevent the lancet 18 from piercing a patient's skin too deeply, and allow deeper penetration for patient's with thicker skin or less blood circulation. This mechanism includes a knob configured to adjust to an arm to physically stop the lancet from protruding past a certain distance. The mechanism can alternatively include a stopper adjustable by a sliding mechanism.

Figure 2B:
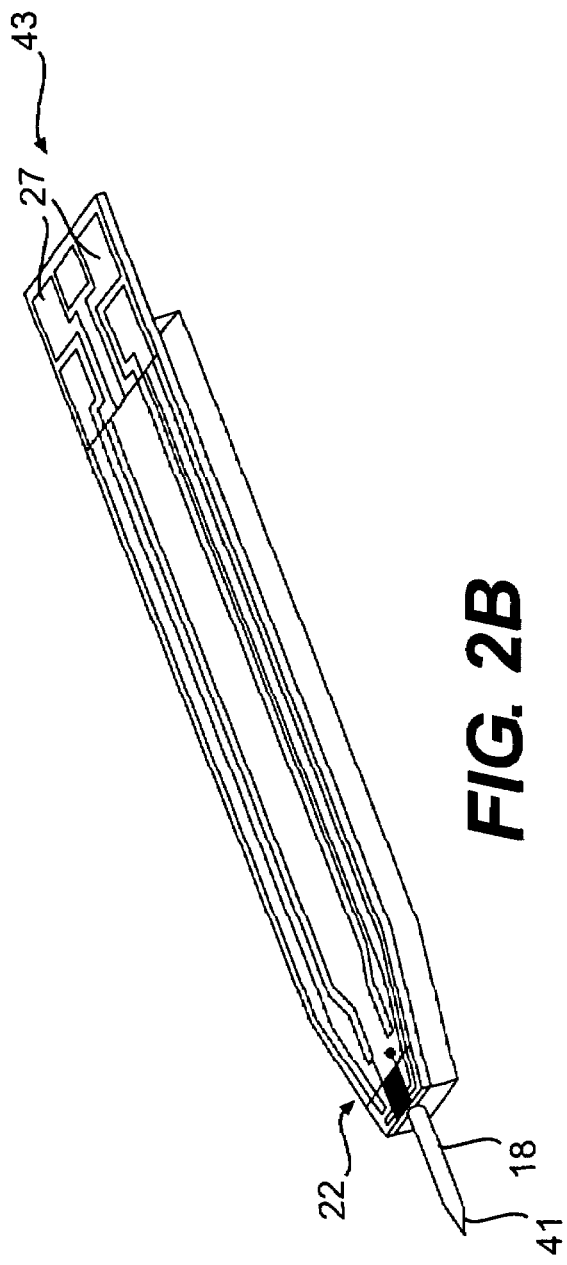
FIG. 2B illustrates a perspective view of the test strip of FIG. 2A, according to an exemplary disclosed embodiment.
Figure 2C:
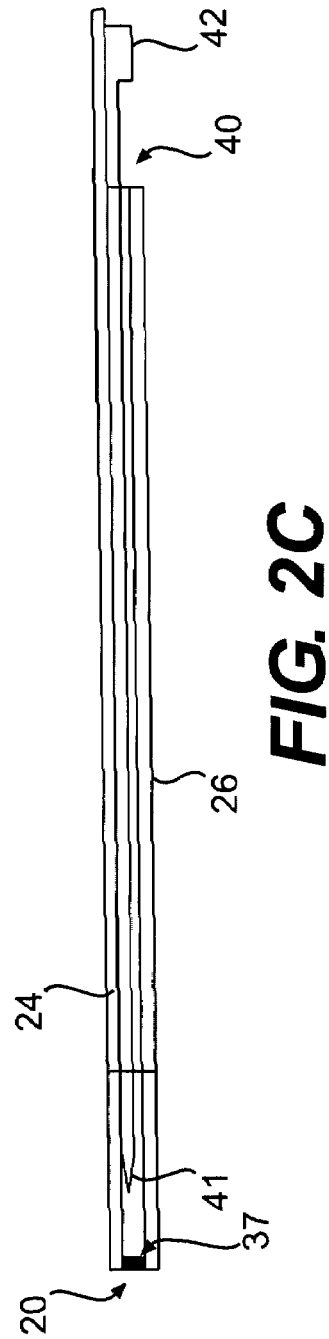
FIG. 2C illustrates a side view of the test strip of FIG. 2A, according to an exemplary disclosed embodiment.

FIGS. 2B and 2C show the test strip 16 with integrated lancet 18 mated to an actuation mechanism 21 in the analyte meter 10. As noted previously, the lancet 18 can be advanced through the opening 20 at the distal end 54 of the test strip 16 in order to pierce the skin of a patient proximate the opening 20. For example, FIG. 2B shows the sharp, pointed end 41 of the lancet 18 pushed out of the test strip 16 by the actuation mechanism 21. Further, as shown in FIG. 2C, the lancet 18 may be retracted into the test strip 16 after piercing a patient's skin, thereby preventing further exposure of the sharp point 41 to a patient.

The lancet 18 in the test strip 16 can be made of a biocompatible plastic or a biocompatible metal. The biocompatible plastic can include a number of suitable types of polymeric materials including, but not limited to, thermosets, elastomers, or other polymeric materials. Further, suitable biocompatible metals can include, for example, stainless steel, titanium, etc. In addition, the lancet 18 can also be formed from various composite materials.

The lancet 18 may be manufactured using a number of suitable production processes. For example, the lancet can be fabricated using known metal processing techniques, such as casting or forging, or for the case of polymeric materials, any suitable polymer processing system can be used, including, for example, injection molding.

As noted previously, the lancet 18 can have a sharp, pointed end 41 that can be used to pierce a patient's skin in order to collect blood. The test strip end 43 that will be engaged with the analyte meter can include a hole 40 for the lancet's mating end 42. The lancet's mating end 42 will be configured to engage the actuation mechanism 21 in the analyte meter 10.

In some embodiments, the test strip 16 can include a membrane 37 that covers and fluidly seals the opening 20. The membrane 37 may help secure the lancet 18 in the cavity 17 until the lancet 18 is needed for use. Further, the membrane 37 can prevent the lancet from becoming contaminated during storage. The membrane 37 can include a variety of suitable materials. For example, the membrane 37 can include any suitable polymer or composite material that can be pierced by the lancet 18 when the lancet 18 is actuated by the actuation mechanism 21. The covering 37 may be impermeable or semipermeable to gas or liquid. For example, suitable materials include polymer thin films, polyethylene, latex, etc.

FIG. 2B illustrates a perspective view of the test strip of FIG. 2A, according to an exemplary disclosed embodiment. As shown, the strip 16 can include a reaction test site 22 configured to receive a blood sample collected after piercing a patient's skin with the lancet 18. The test site 22 can include one or more substances configured to react with one or more analytes. For example, the reaction test site 22 may include one or more enzymes configured to react with an analyte such as glucose. Furthermore, the reaction test site 22 may include other additives, including salts, buffers, enzyme stabilizers, electrochemical mediators, color indicators, and/or any other chemical needed to facilitate production of a suitable test reaction.

The reaction test site 22 may have a shape and size configured to hold certain substances needed to react with an analyte to be tested. For example, the reaction test site 22 may include a well configured to secure a certain sample volume. In addition, the reaction test site 22 may include various configurations that can facilitate sample acquisition, proper sample placement, or needed fluid flow.

In addition, the test strip 16 can include one or more electrodes 27. These electrodes 27 can be configured to engage corresponding electrodes on an analyte test meter to form an electrical connection with the test meter 10, thereby allowing a reaction that occurs at the test site 22 to be correlated with a blood analyte concentration.

It should be noted that although the test strip 16 is shown as a rectangularly shaped strip, the test strip 16 can include a variety of suitable shapes and sizes as long as the test strip 16 can include an elongate cavity 17 and lancet 18. For example, the test strip 16 can be in the form of ribbons, tabs, discs, or any other suitable form. Further, as noted above, the test strip 16 can also be configured for use with a variety of suitable testing modalities, including electrochemical tests, photochemical tests, electrochemiluminescent tests, and/or any other suitable testing modality.

FIG. 2C illustrates a side view of the test strip of FIG. 2A, according to an exemplary disclosed embodiment. As shown, the test strip 16 has a first test strip substrate 24 and a second test strip substrate 26 that form the bottom or the top portions of the test strip 16. In some embodiments, the test strip substrates 24, 26 can be formed separately and then attached to one another. For example, the substrates 24, 26 can be attached to one another using glue, epoxy, or mechanical attachments (e.g. pins, clips etc). Further, in some embodiments the test strip substrates 24, 26 may be welded, burned, or attached to one another using any other suitable thermal, mechanical, or chemical methods.

The test strip substrates 24, 26 can be produced from a variety of suitable material types. For example, in some embodiments, the test strip substrates 24, 26 can include suitable plastics, metals, ceramic, and/or composite materials. Substrates 24, 26 may be selected based on a variety of factors, including for example, cost, processing, feasibility of sterilization, mechanical properties, and effects on enzymes, mediators, or other chemicals needed to produce a suitable reaction. Further, suitable substrates can include a single layer material or multi-layered material.

Figure 3:
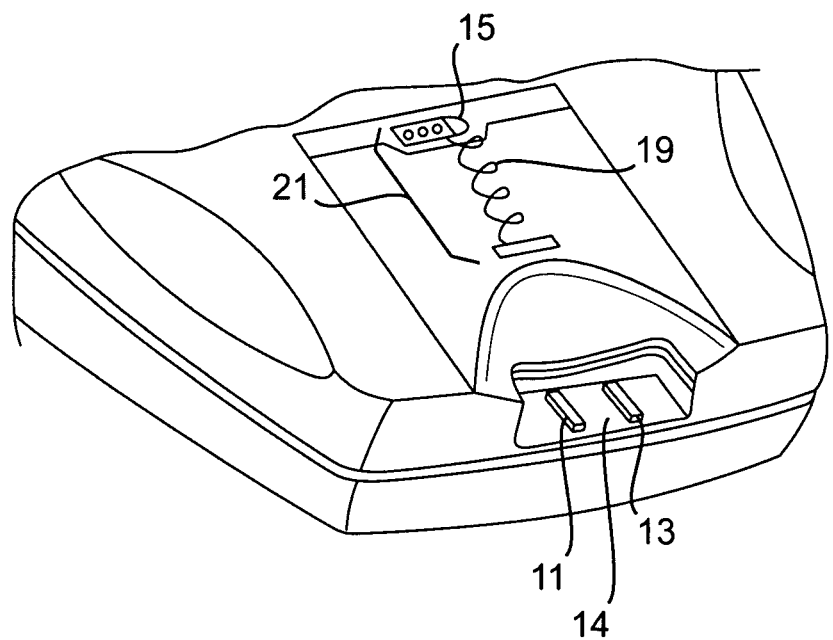
FIG. 3 illustrates a perspective view of a test meter including a lancet actuation mechanism, according to an exemplary disclosed embodiment.

In some embodiments, the analyte test meter 10 of the present disclosure can include an actuation mechanism 21 configured to advance the lancet 18 through the opening 20 in the test strip 16 in order to pierce a patient's skin. FIG. 3 illustrates a perspective view of an exemplary embodiment of a test meter 10 with an actuation mechanism 21. As shown, the actuation mechanism 21 can include a spring 19 configured to quickly push the lancet 18 in and out of the opening 20. The spring 19 can include a variety of suitable spring types, including buckling columns, nested compression springs, conical springs, variable-pitch springs, snap-rings, double torsion springs, wire forms, limited-travel extension springs, braided-wire springs, etc. Further, the spring can be produced from any of a number of metals, plastics, or composite materials.

Further, although as shown, the actuation mechanism 21 is a spring-driven actuation mechanism any suitable actuation mechanism can be used. For example, as shown, actuation mechanism 21 may alternatively or additionally include a motor, such as an electric motor that may control movement of the spring 19 or directly engage the lancet 18. Further, other suitable actuation mechanisms can include a solenoid or other linear actuator, which may advance and retract suitable materials having certain magnetic properties.

Figure 4:
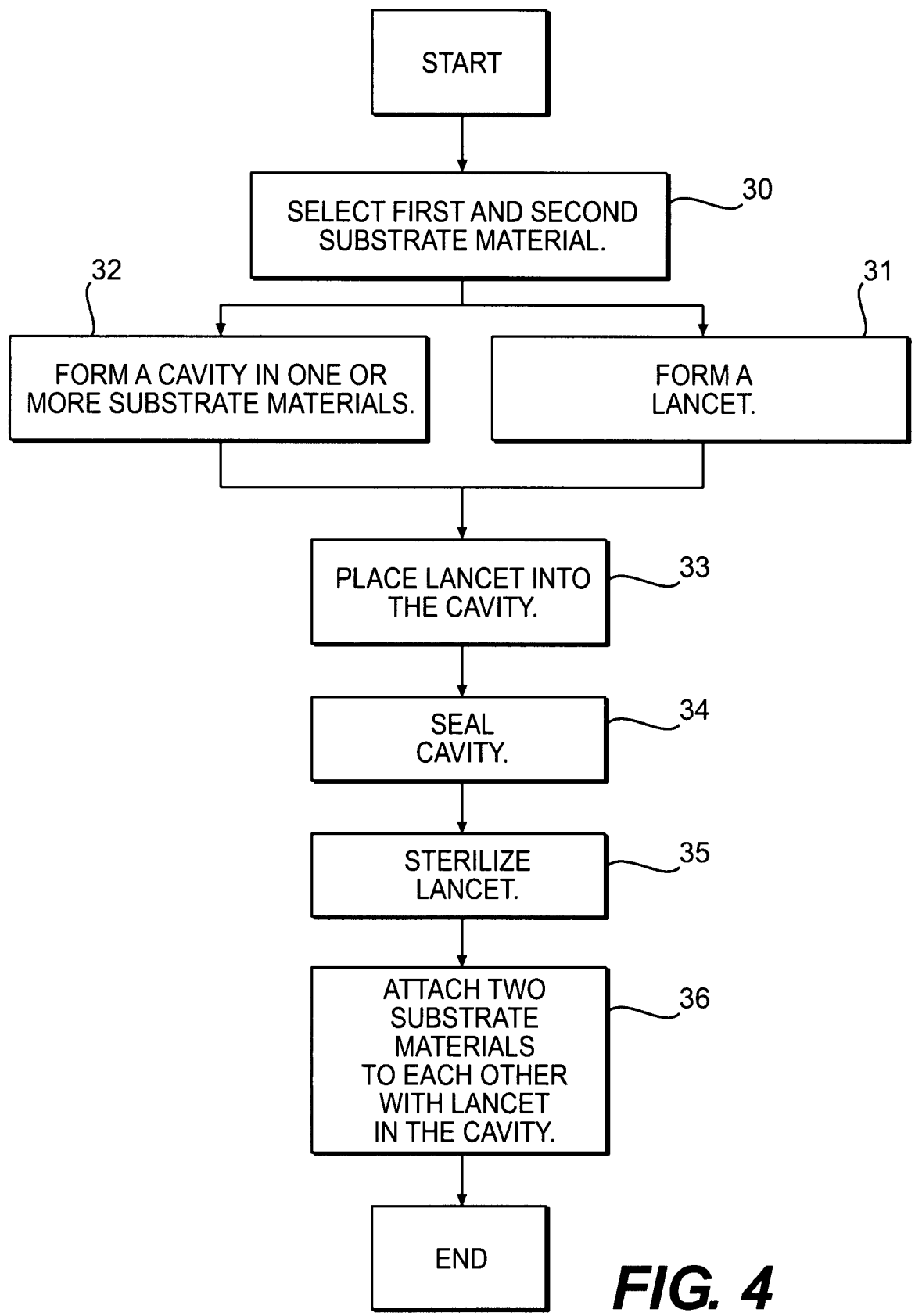
FIG. 4 illustrates a flow chart of a process for producing a test strip with an integrated lancet, according to an exemplary disclosed embodiment.

The disclosed test strip 16 with the integrated lancet 18 can be produced using a number of suitable fabrication processes. For example, FIG. 4 illustrates a flow chart of a method of making a test strip with an integrated lancet 18, according to an exemplary disclosed embodiment. As shown at Step 30, first and second substrate materials 24, 26, are first selected. As noted above, these substrate materials can be selected from a variety of different plastics, polymers, metals, ceramics or composite materials. Next, as shown at Step 31, a lancet 18 may be produced with a sharp distal end 41 and a proximal end 42 configured to engage a meter actuation system.

Next, as shown at Step 32, a cavity 17 may be formed in one or more substrates 24, 26. The cavity 17 can be formed using a number of suitable production processes. For example, the cavity 17 can be etched using a laser or water-jet cutter. The cavity 17 can also be formed using a chemical that chemically reacts with at least one of the test strip substrates 24, 26 to remove a selected portion of the substrate, thereby forming a cavity in the substrate. In addition, the cavity 17 can also be formed by using a saw or another cutting tool to cut out a cavity from at least one of the test strip substrates 24, 26. Any suitable method may be selected as long as the cavity has a size and shape configured to hold the lancet 17 and allow the lancet to be moved in and out of the opening 20 to pierce a patient's skin.

Next, as shown at Step 33 the lancet 18 is placed into the cavity 17, and the cavity 17 may be fluidly sealed, for instance with a membrane 37, as shown at step 34. After sealing the opening 20 hermetically with the membrane 37, the lancet 18 and/or substrate 26 in which the lancet is contained can be sterilized. The lancet 18 may be sterilized, before the test strip 16 is completed, or alternatively, the lancet 18 may be sterilized before sealing the opening 20 or before placement within the cavity 17, as long as the final product will be suitably sanitary for patient use. The lancet may be sterilized after being disposed in first or second substrate material along with the one first or second substrate. Further, in some embodiments, the entire test strip 16, including both test strip substrates 24, 26 may be sterilized in one step after the first and second substrate 24, 26 are attached to one another. In this case, the sterilization process may be performed before application of selected enzymes or mediators, or using a process that will not damage the enzymes or mediators. The lancet may be sterilized using a number of different sterilization techniques including, for example, autoclaving, radiation, ethylene oxide, and ethyl alcohol.

The test strip of the present disclosure is straightforward to use. First, a person will engage the test strip 16 with the meter interface 14 to secure the strip in place and form a connection between the electrical components and the test strip lancet and meter actuation system. Next, the user will place his or her skin proximate the test strip opening 20 and actuate the lancet using the meter to pierce the skin and obtain a sample of blood. The blood will be collected on the sample reaction site 22, and the analyte meter 10 will then analyze the blood for analyte concentration and display the results on the display unit 12.

A feature of the present test strip with integrated lancet is the consolidation of the testing components into a single disposable test strip device 16. The consolidated test strip and meter with actuation system provide a more convenient and user friendly system with fewer components. Having a lancet 18 incorporated into a test strip 16 ensures that a patient will use a single lancet 18 only once before disposing it. This method allows the patient to use a sterile lancet 18 every time he or she needs to obtain a sample of blood. Using a lancet 18 only once will also lessen the pain the patient might feel as he or she will use a new, sharp lancet each time rather than re-using the same lancet that might have become dull over time.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

LIST OF ELEMENTS

Title

Test Strip with Integrated Lancet 10 analyte meter
11 electrode
12 display system
13 electrode
14 test strip interface
15 motor
16 test strip
17 cavity
18 lancet
19 spring
20 opening for lancet's sharp end
21 actuation mechanism
22 reaction test site
24 first test strip substrate
26 second test strip substrate
27 test strip electrodes
30 step of selecting first and second substrate
31 step of forming a lancet
32 step of forming a cavity in one or more substrate
33 step of placing lancet into the cavity
34 step of sealing the cavity
35 step of sterilizing the lancet
36 step of attaching two substrates to each other with lancet in the cavity
37 thin film covering opening of lancet
40 opening for lancet's mating end
41 sharp end (distal end of lancet)
42 lancet's mating end (proximal end of lancet)
43 second end of test strip
54 first end of test strip

The invention claimed is:

1. An analyte test strip comprising:
a first test strip substrate having a bottom surface;
a second test strip substrate having a top surface;
a reaction test site located on at least one of the first substrate and the second substrate;
an elongate cavity extending between the bottom surface of the first substrate and the top surface of the second substrate and traversing the reaction test site;
a lancet having a pointed end and an opposite end configured to engage an actuation mechanism of an analyte meter, the lancet disposed in the elongate cavity;
the first and second test strip substrates mated to each other, sealing the cavity therebetween, wherein a proximal end of one of the first and the second substrates extends beyond a proximal end of the other of the first and the second substrates and is configured to engage an interface of the analyte meter to form an electrical connection between the test strip and the meter, and wherein the cavity extends to the proximal end of the other of the first and the second substrates;
an opening of the cavity disposed at one end of the test strip and positioned proximate to the reaction test site; and
a seal configured to seal the opening, wherein the pointed end of the lancet is movable in and out of the opening and traversing the seal.

2. The test strip of claim 1, wherein the lancet comprises at least one of a biocompatible plastic and a biocompatible metal.

3. The test strip of claim 1, wherein the reaction test site comprises one or more enzymes selected to facilitate a reaction with glucose.

4. The test strip of claim 3, wherein the one or more enzymes comprise at least one of glucose oxidase and glucose dehydrogenase.

5. The test strip of claim 1, wherein the seal covering the opening is comprised of a thin film.

6. The test strip of claim 5, wherein the thin film is comprised of a polymer.

7. The test strip of claim 5, wherein the thin film is comprised of a latex.

8. The test strip of claim 5, wherein the thin film is comprised of a polyethylene.

9. An analyte meter for monitoring a characteristic of a sample of blood, comprising:
a test strip interface for engaging a first end of a test strip, the test strip including:
a first test strip substrate having a bottom surface;
a second test strip substrate having a top surface;
a reaction test site located on at least one of the first substrate and the second substrate;
an elongate cavity extending between the bottom surface of the first substrate and the top surface of the second substrate and traversing the reaction test site;
a lancet having a pointed distal end opposite a proximal end, the proximal end configured to engage an actuation mechanism of an analyte meter, the lancet disposed in the elongate cavity;
the first and second test strip substrates mated to each other, sealing the cavity therebetween, wherein a proximal end of one of the first and the second substrates extends beyond a proximal end of the other of the first and the second substrates at the first end of the test strip;
an opening of the cavity disposed at one end of the test strip;
a seal configured to seat the opening; and
the opening positioned proximate to the reaction site, wherein the distal end of the lancet is movable in and out of the opening and traversing the seal;
an actuation mechanism configured to engage the proximal end of the lancet and to advance the distal end of the lancet through the opening of the test strip;
a test strip interface configured to engage the proximal end of one of the first and the second substrates aired that extends beyond the other of the first and the second substrates to form an electrical connection between the test strip and the analyte meter, and
wherein the cavity extends to the proximal end of the other of the first and the second substrates; and
a meter for measuring the concentration of an analyte in a sample of blood.

10. The analyte meter of claim 9, wherein the actuation mechanism comprises a spring.

11. The analyte meter of claim 9, wherein the actuation mechanism comprises a motor.

12. The test strip of claim 1, wherein the pointed end of the lancet is configured to protrude a predetermined distance from the opening.

* * * * *